United States Patent [19]

Oosten

[11] 4,378,801
[45] * Apr. 5, 1983

[54] ELECTROSURGICAL GENERATOR

[75] Inventor: Roger L. Oosten, New Port Ritchey, Fla.

[73] Assignee: Medical Research Associates Ltd. #2, Clearwater, Fla.

[*] Notice: The portion of the term of this patent subsequent to Mar. 9, 1999, has been disclaimed.

[21] Appl. No.: 215,046

[22] Filed: Dec. 10, 1980

Related U.S. Application Data

[63] Continuation-in-part of Ser. No. 104,692, Dec. 17, 1979, Pat. No. 4,318,409.

[51] Int. Cl.³ .............................................. A61B 17/39
[52] U.S. Cl. .......................... 128/303.14; 128/303.17
[58] Field of Search .................. 128/303.13, 303.14, 128/303.17, 303.18

[56] References Cited

U.S. PATENT DOCUMENTS

| | | | |
|---|---|---|---|
| 3,801,800 | 4/1974 | Newton | 128/303.14 |
| 3,885,569 | 5/1975 | Judson | 128/303.14 |
| 4,051,855 | 10/1977 | Schneiderman | 128/303.14 |
| 4,071,028 | 1/1978 | Perkins | 128/303.14 |
| 4,094,320 | 6/1978 | Newton et al. | 128/303.14 |
| 4,123,673 | 10/1978 | Gonser | 128/303.14 X |
| 4,154,240 | 5/1979 | Ikuno et al. | 128/303.14 |
| 4,171,700 | 10/1979 | Farin | 128/303.14 |

*Primary Examiner*—Lee S. Cohen
*Attorney, Agent, or Firm*—Gipple & Hale

[57] ABSTRACT

A fixed high frequency oscillator, variable frequency divider, and low frequency timer are provided to produce a high frequency output pulse group which is terminated at different intervals by both the variable frequency divider and the timer. The characteristics of the frequency divider may be varied to produce a number of modes of generator operation, all of which utilize a single high frequency output. The generator includes apparatus for producing a voltage spike as one of the pulses of each output group with a crest ratio of at least 3:1 in the cut command group and at least 14:1 in the fulgurate mode. The spike reionizes the current path through tissue without excessive tissue destruction due to wasted power and is minimized in dessicate mode where reionization arcing is undesirable. A pair of opto-isolated hand-held switches allow the user to select continuously between two preset modes of operation without risking shock.

14 Claims, 15 Drawing Figures

_Fig. 14_

_Fig. 15_

_4,378,801_

ELECTROSURGICAL GENERATOR

RELATED APPLICATIONS

This is a continuation-in-part of U.S. patent application Ser. No. 104,692 filed Dec. 17, 1979, now U.S. Pat. No. 4,318,409, issued Mar. 9, 1982.

BACKGROUND OF THE INVENTION

This invention relates to an electrosurgical generator, and more specifically to an electrosurgical generator which selectively generates a variety of coagulate signals and cutting signals.

Past electrosurgical generators normally produced a variety of signals and have controls to adjust signal strength and other parameters of operation. One problem with past electrosurgical generators has been that the multiplicity of controls impaired the treating physician's ability to switch rapidly from one signal mode to another, a particularly crucial problem when medical exigencies require rapid response. Since such controls are most useful when placed within easy reach of operating personnel, isolation from shock hazard is very important, not only for the patient, but also for the physician. Past generators have typically used only a single isolation transformer with the side taps coupled through blocking capacitors to the output terminal. This isolation scheme has often proved inadequate to eliminate the danger of electric shock. For a discussion of the prior art of isolation, see the U.S. Pat. No. 4,094,320 assigned to Valleylab, Inc.

Furthermore, past electrosurgical generators have produced a simultaneous cutting and coagulating effect, known in the art as a blend signal, by literally blending a cut signal and a coagulate signal. Since significantly different signal levels are required to produce comparable levels of effectiveness between these two signals, past generators have included complex hardware to accomplish an effective literal blending. See, for example, the U.S. Pat. No. 4,154,240.

Incisions created by electrosurgical generators are based on the creation of an ionization path between the closely-spaced electrodes of the electrosurgical scalpel. Past generators have normally utilized high power output levels to maintain an active ionization path, which not only required a massive power supply and generating hardware, but also dissipated waste heat along the incision, and disrupted tissue unnecessarily. A typical prior art electrosurgical incision of the skin would therefore cause a continuous explosive sputtering of the fat layer directly underneath the skin, and the skin incision would heal slowly to produce substantial scar tissue. Users of prior art electrosurgical generators would typically make an initial incision through the skin and fat layer with the traditional knife scalpel in order to avoid this problem.

Some prior art generators have featured a constant-current output amplifier in order to produce a uniform electrosurgical effect over a fairly broad range of tissue impedance. See U.S. Pat. No. 3,601,126 for an output feedback system to maintain constant output levels. Where differing signal frequencies were used as the basis for different generator output modes, the change in frequency would change the output impedance of the amplifier. In this regard see U.S. Pat. No. 3,699,967, assigned to Valleylab, Inc. Thus, past generators with constant-current output amplifiers were in fact limited to a fairly narrow range of tissue types and incision techniques.

SUMMARY OF THE INVENTION

In accordance with the present invention there is provided a fixed high frequency oscillator, a variable frequency divider, a low frequency oscillator or timer, means for interrupting the fixed high frequency oscillator output signal using both the frequency divider and the timer and means for altering the interruption pattern of the frequency divider in order to produce a pure cut, blend, fulgurate or desiccate output signal. One pulse of each output pulse group is an extremely narrow voltage spike which re-establishes the ionization path through local tissues anomalies such as gristle in normal non-homogenous human tissue. The high ratio of peak power to RMS power in this pulse spike allows re-ionization without harmful dissipation of excess power through tissue. The remaining pulses of each output pulse group are of uniform peak voltage substantially lower than the peak of the previous voltage spike and the output pulse group as a whole produces an incision using minimal electrical power and which will heal rapidly with minimal scar tissue. Repeated re-ionization using the voltage spike makes the present invention especially useful for initial incisions through skin and fat layers without sputtering, which avoids the need for a starter incision made by a knife scalpel.

Because the four modes of operation of the present invention are based on the use of a single fixed high frequency oscillator to generate an output signal, the impedance of the output amplifier is not significantly affected by variation in output frequency. The present invention is therefore more useful than the prior art over a wide variety of application parameters including electrode types, human tissue impedance variation, and differences in incision motions used by treating physicians. Users find that less practice is required with the present invention than with the prior art in order to learn an effective incision stroke.

The present invention also provides isolation from shock hazard at a plurality of points in the generator. The hand-held control switches are isolated from the command control using a small dedicated power supply and an opto-isolator. The output of the interrupt means is coupled to the input of the main amplifier through a blocking capacitor to block spurious D.C. current from passing to the patient, and various stages of the output amplifier are isolated from one another and from the output terminals by isolation transformers.

DETAILED DESCRIPTION OF THE DRAWINGS

The best mode and preferred embodiment of the invention is shown in FIGS. 1 through 6 and 8 and comprises a signal generator circuit generally indicated at 10 to selectively generate a pure cut signal, a blend signal, a fulgurate signal, or a desiccate signal. These four modes of operation are treated as two command groups: the cut command includes the pure cut and blend modes, while the coagulate command includes the fulgurate and desiccate modes. The treating physician may continuously select either the cut command or the coagulate command using the hand switches 510 and 511 or the foot switches 512 and 513. The hand switches, which are most likely to come into electrical contact with the patient or physician during normal use, are isolated from the bulk of the electric circuit by isolation circuit 101. If both the cut and the coagulate commands are selected simultaneously by the physician, the command control 103 will shut off all functions until the command ambiguity is resolved. Otherwise, the command control 103 activates command line 201 if the cut command is chosen, or command line 202 if the coagulate command is chosen.

Figure 1:
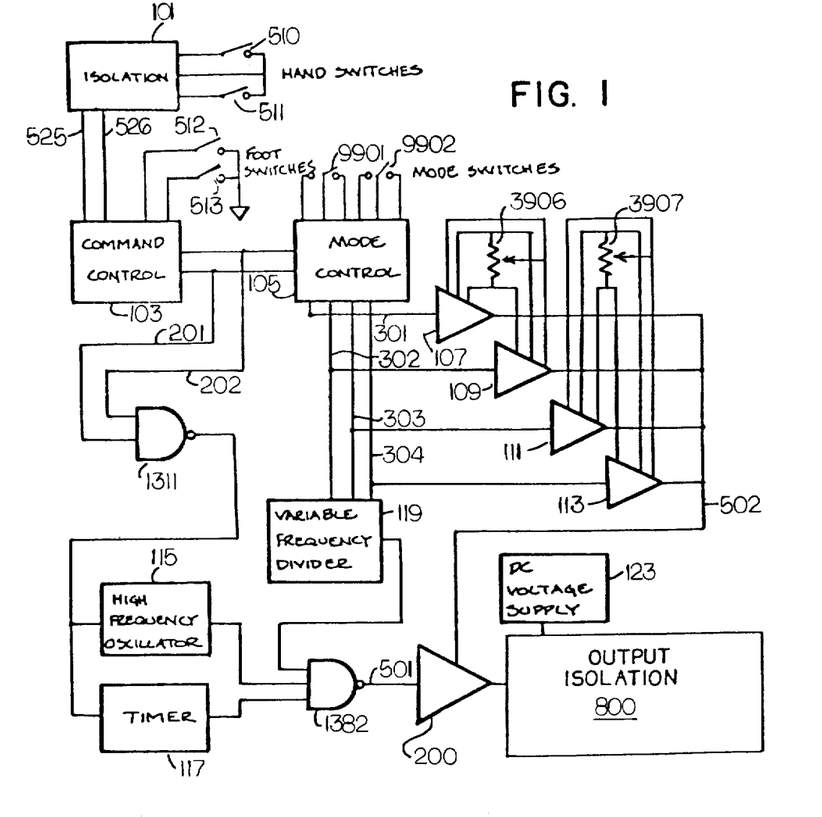
FIG. 1 is a partial block diagram and partial circuit diagram showing one example of the electrosurgical generator according to this invention.
Figure 3:
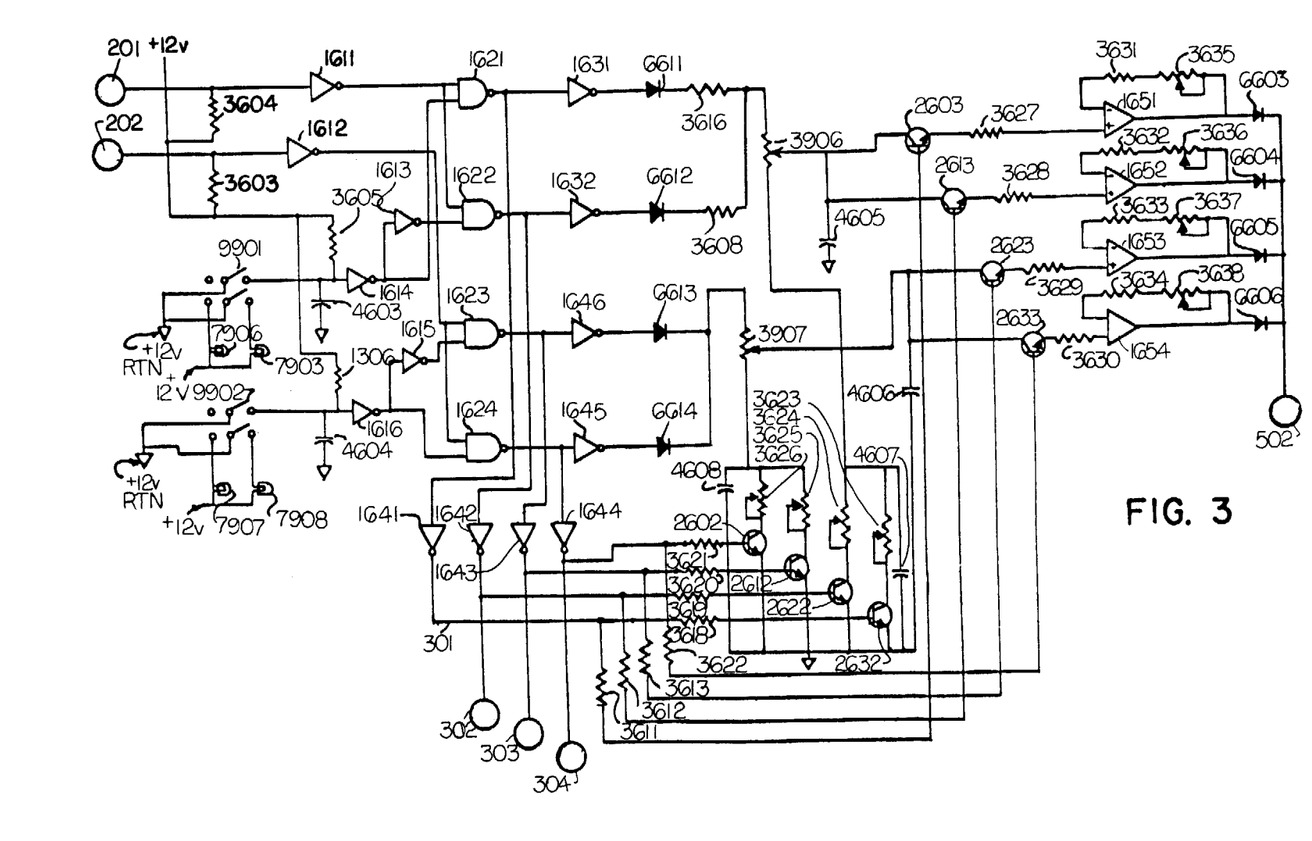
FIG. 3 is a circuit diagram of the mode control 105 and output control amplifier 107, 109, 111, and 113 of FIG. 1.

The command line thus activated will in turn activate one of the two mode switches 9901 or 9902 which are part of the mode control 105. Switch 9901 is enabled by the cut command line 201 and allows the operator to choose between the two cut modes: pure or blend. Switch 9902 is enabled by the coagulate line 202 and allows the operator to choose between the two coagulate modes: desiccate or fulgurate. Since only one of the two command lines are active at any moment, only one of the four mode lines 301, 302, 303, and 304 will be activated by the mode control 105 at any moment.

The active mode line enables one of the four output control amplifiers 107, 109, 111, and 113. These amplifiers produce a voltage controlling the output gain of the main amplifier 200. Amplifiers 107 and 109 control the cut modes output levels and are controlled by potentiometer 3906. Amplifiers 111 and 113 control the output level for the two coagulate functions and are controlled by potentiometer 3907.

Figure 7:
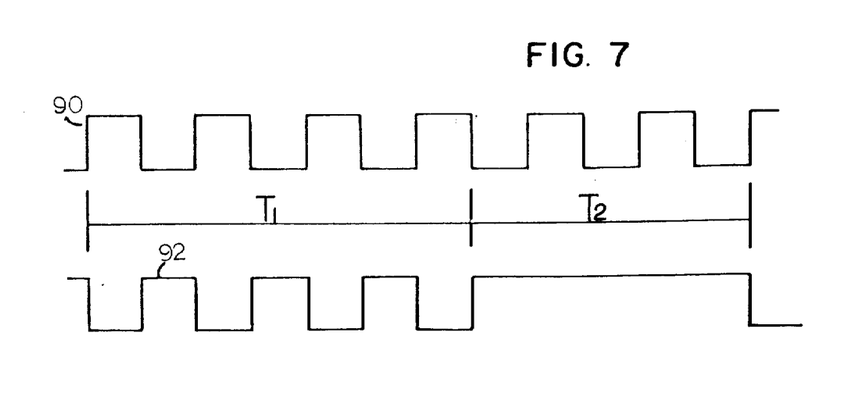
FIG. 7 is a diagram of the wave form of the high frequency oscillator 115 and the variable frequency divider 119 of FIG. 1.

Activation of either of the two command lines 201 or 202 will cause NAND gate 1311 to activate the fixed high frequency oscillator 115 and the timer 117. The output of fixed high frequency oscillator 115, preferably 450 KHz, passes through NAND gate 1382 to reach the main amplifier 200. The variable frequency divider 119 produces the primary modulation of the high frequency signal by counting the output pulses of the fixed high frequency oscillator 115 and periodically interrupting the output of NAND gate 1382. FIG. 7 shows the interruption pattern $T_1+T_2$ of high frequency oscillator output 90 produced by divider 119. The uninterrupted period $T_1$ of NAND gate 1382 output determines the duration of the output pulse group and is chosen by the activated mode line, and the repetition period of $T_1+T_2$ is a fixed multiple of the wavelength of high frequency oscillator output 90. The resulting output waveform of NAND gate 1382 is shown at 92.

The output of NAND gate 1382 is also interrupted periodically by timer 117 to produce a secondary modulation of the high frequency signal. The timer operates at a fixed frequency much lower than that of the fixed high frequency oscillator 115 and the variable frequency divider 119, preferably 5 KHz.

The output of NAND gate 1382 is fed to the input of main amplifier 200. As previously stated the output level of the main amplifier 200 is set by the output of the activated output control amplifier. The main amplifier output draws current from the D.C. voltage source 123 through the output isolation 800. The treating physician may choose between bipolar and monopolar output configuration by making appropriate connections between the patient electrodes and the output isolation 800.

Figure 8:
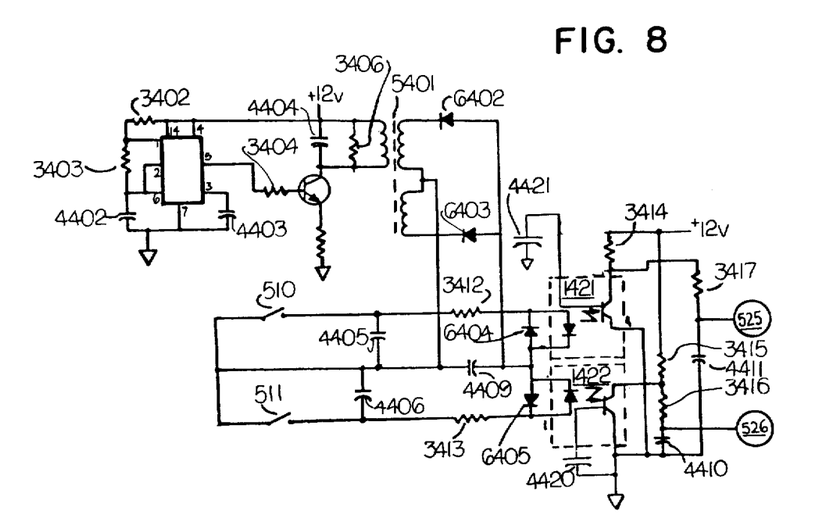
FIG. 8 is a circuit diagram of the isolation 101 of FIG. 1.
Figure 9:
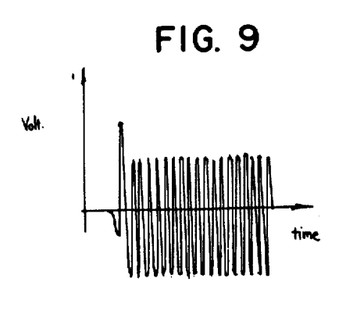
FIG. 9 is a diagram of the output wave form of the generator in pure cut mode.
Figure 10:
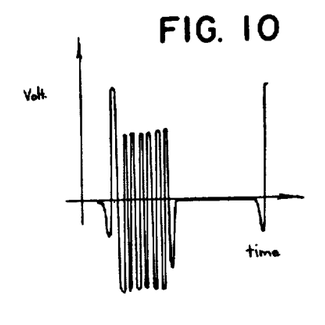
FIG. 10 is a diagram of the output wave form of the electrosurgical generator in blend mode.
Figure 11:
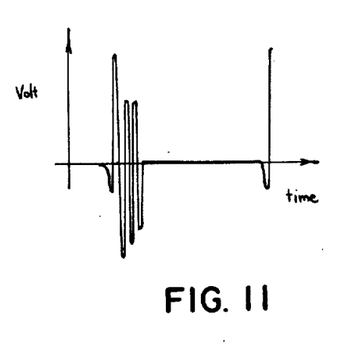
FIG. 11 is a diagram of the output wave form of the electrosurgical generator in desiccate mode.
Figure 12:
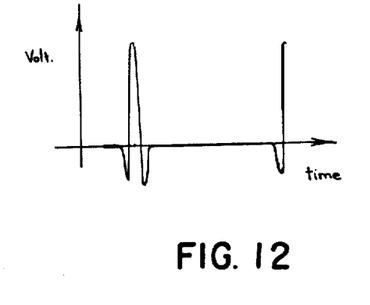
FIG. 12 is a diagram of the output wave form of the electrosurgical generator in fulgurate mode.

FIG. 8 illustrates an isolation circuit 101 which isolates and reduces RF leakage between hand-held command switches 510, 511 and the command control 103. The isolation circuit consists of an audio frequency oscillator, preferably running at 23 KHz, which pulses transistor 2401. The oscillator is formed by integrated circuit 1411, typically a type 556 timer with 12 volts supplied to pins 4 and 14. Resistor 3402 connects pins 14 and 1; resistor 3403 connects pin 1 to pins 2 and 6. Capacitor 4402 connects pin 6 to ground, capacitor 4403 connects pin 3 to ground, and pin 7 is grounded directly.

The output of integrated circuit 1411 passes from pin 5 through resistor 3404 to the base of transistor 2401. Resistor 3405 couples the emitter of transistor 2401 to ground, and the collector of transistor 2401 is coupled to the 12 volt supply through capacitor 4404, resistor 3406, and the primary winding of transformer 5401 in parallel. As the oscillator pulses transistor 2401, current is alternately blocked or drawn through the primary winding of transformer 5401. The cathodes of diodes 6402 and 6403 are coupled to te side taps of the secondary winding of transformer 5401. Capacitor 4409 couples the center tap of the secondary winding of transformer 5401 to the anodes of diodes 6402 and 6403. The center tap is further coupled directly to the common line connecting hand switches 510 and 511. Capacitor 4405 couples the center tap of the secondary winding of transformer 5401 to switch 510 and resistor 3412. Switch 510 is connected through resistor 3412 to pin 1 of opto-isolator 1421. Diode 6404 is connected between pins 1 and 2 of opto-isolator 1421; pin 2 is also connected to anodes of diodes 6402 and 6403.

Similarly, capacitor 4406 couples the center tap of the secondary winding of transformer 5401 to switch 511 and resistor 3413. Switch 511 is connected through resistor 3413 to pin 1 of opto-isolator 1422; pin 1 is also connected through diode 6405 to pin 2, to pin 2 of opto-isolator 1421 and to the anodes of diodes 6402 and 6403.

Opto-isolator 1421 is grounded to the output circuit ground at pin 4. Pin 5 is the output for switch 510, and is connected through resistor 3414 to a 12 volt supply, through resistor 3417 to line 525, and through resistor 3417 and capacitor 4411 in series to ground. Pin 6 is coupled through capacitor 4421 to ground. Likewise, opto-isolator 1422 is grounded to the output circuit ground at pin 4. Pin 5 is the output for switch 511, and is connected through resistor 3415 to a 12 volt supply, through resistor 3416 to line 526, and through resistor 3416 and capacitor 4410 in series to ground. Pin 6 is coupled through capacitor 4420 to ground.

The secondary voltage of the transformer is full wave rectified and filtered to a D.C. voltage by diodes 6402 and 6403 and capacitor 4409. Resistors 3412 and 3413 limit the small amount of D.C. current supplied to the hand switches and the input diodes of opto-isolators 1421 and 1422. For example, when the cut command group is activated by closing switch 510, current flows through resistor 3412 and pins 1 and 2 of opto-isolator 1421 which causes the output of the opto-isolator 1421 to go low.

Figure 2:
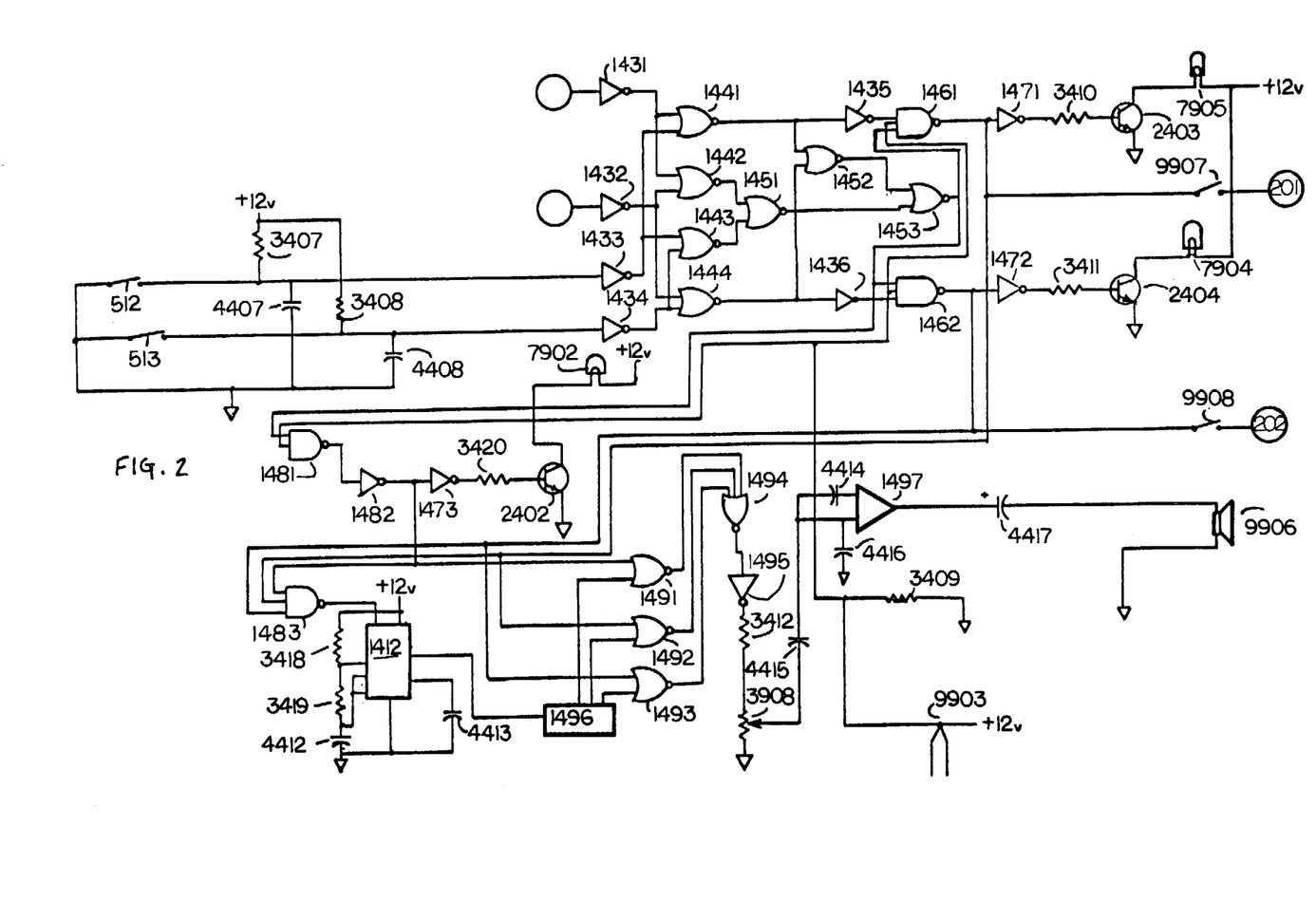
FIG. 2 is a circuit diagram showing the command control 103 of FIG. 1.

Referring now to FIG. 2, the inputs of inverters 1431 and 1432 are connected to the hand switches 510 and 511, respectively, via isolation 101 and lines 525 and 526 respectively. The input of inverter 1433 is coupled through switch 512 and capacitor 4407 in parallel to ground, and through resistor 3407 to a 12 volt supply. Likewise, the input of inverter 1434 is coupled through switch 513 and capacitor 4408 in parallel to ground and through resistor 3408 to a 12 volt supply. Therefore, the inputs of inverters 1433 and 1434 will remain at high value unless a switch is closed, at which time the respective inverter input will go low and its output will go high.

The outputs of inverters 1431 and 1433 are coupled directly to the inputs of NOR gate 1441. Therefore, when either or both of switches 510 and 512 are opened, the output of NOR gate 1441 will be low. The outputs of inverters 1432 and 1434 are coupled directly to the inputs of NOR gate 1444. Therefore, when either or both of switches 511 and 512 are opened, the output of NOR gate 1444 will be low.

The outputs of inverters 1431 and 1432 are also coupled to the inputs of NOR gate 1442. When either or both of switches 510 and 511 are closed, the output of NOR gate 1442 will go low. The output of inverters 1433 and 1434 are coupled to the inputs of NOR gate 1443. When either or both of switches 510 and 511 are opened, the output of NOR gate 1443 will go low. The outputs of NOR gates 1442 and 1443 are coupled to the inputs of NOR gate 1451, and the outputs of NOR gates 1441 and 1444 are coupled to the inputs of NOR gate 1452. The outputs of NOR gates 1451 and 1452 are coupled to the inputs of NOR gate 1453.

The cut command may be indicated by closing either of switches 510 or 512, and the coagulate command may be indicated by closing either of switches 511 or 513. When any two switches are closed indicating conflicting operation modes at the same time, the output of NOR gate 1453 will go low.

The output of NOR gate 1441 is coupled through inverter 1435 to one input of NAND gate 1461. The output of NOR gate 1453 is connected to another input of NAND gate 1461, and the output of thermostat 9903 is coupled to a third input of NAND gate 1461. Thus, when the output of inverter 1435 is high, indicating cut command, and the output of NOR gate 1453 is high, indicating no conflicting command, and the out-put of thermostat 9903 is high, indicating no heat overload, then the output of NAND gate 1461 will be low activating the command line 201 through switch 9907. If the output of NOR gate 1453 goes low or the output of thermostat 9903 goes low, the output of NAND gate 1461 goes high, deactivating command line 201.

The output of NAND gate 1461 is also coupled through inverter 1471 and resistor 3410 in series to the base of transistor 2403. The emitter of transistor 2403 is grounded and the collector of transistor 2403 is coupled through lamp 7903 to a 12 volt supply. When NAND gate 1461 activates command line 201, the base of transistor 2403 goes high, drawing current through lamp 7903 which lights to indicate cut command group operation to the treating physician.

Similarly, the output of NOR gate 1444 is coupled through inverter 1436 to one input of NAND gate 1462. The output of NOR gate 1453 is connected to another input of NAND gate 1462, and the output of thermostat 9903 is coupled to a third input of NAND gate 1462. When the output of inverter 1436 is high, indicating coagulate command, the output of NOR gate 1453 is high, indicating no conflicting command, and the out-put of thermostat 9903 is high, indicating no heat overload, then the output of NAND gate 1462 will be low, activating the command line 202 through switch 9908. If the output of NOR gate 1453 goes low or the output of thermostat 9903 goes low, the output of NAND gate 1462 goes high, deactivating command line 202.

The output of NAND gate 1462 is also coupled through inverter 1472 and resistor 3411 in series to the base of transistor 2404. The emitter of transistor 2404 is grounded and the collector of transistor 2404 is coupled through lamp 7904 to a 12 volt supply. When NAND gate 1462 activates command line 202, the base of transistor 2404 goes high, drawing current through lamp 7904 which lights to indicate coagulate command group operation to the treating physician.

The output of NOR gate 1453 and thermostat 9903 are also coupled to the inputs of NAND gate 1481. The output of NAND gate 1481 is connected through inverters 1482, 1473, and resistor 3420 in series to the base of transistor 2402. The emitter of transistor 2402 is grounded, and the collector of transistor 2402 is connected through lamp 7902 to a 12 volt supply. If either thermostat 9903 or the output of NOR gate 1453 goes low, then the base of transistor 2402 will go high and current will glow through lamp 7902, indicating to the treating physician that the generator has automatically ceased operation.

The outputs of NAND gate 1461 and 1462 and of inverter 1482 are coupled to the inputs of NAND gate 1483. The output of NAND gate 1483 is connected to pin 10 of integrated circuit 1412. If either command line 201 or 202 is activated, or if the generator is automatically shut down, the output of NAND gate 1483 goes high, activating an oscillator formed by integrated circuit 1412 and associated passive elements. Pin 14 of integrated circuit 1412 is connected to a 12 volt supply, and pin 14 is also connected through resistor 3418 to pin 13. Pin 13 is connected through resistor 3419 to pins 8 and 12. Pin 7 is grounded, and is connected through capacitor 4413 to pin 11. Pin 7 is also coupled through capacitor 4412 to pins 8 and 12. The oscillator output is pin 9 of integrated circuit 1412, which is coupled to the input of binary counter 1496.

Binary counter 1496 divides the output frequency of the oscillator by three different fixed factors. Each of three counter outputs are coupled to an input of NOR gates 1491, 1492, and 1493 respectively. The output of inverter 1482 is coupled to the second input of NOR gate 1491, so that when NOR gate 1453 or thermostat 9903 cause a shutdown, the output of NOR gate 1491 will be the inverse of the associated input from the counter 1496. Likewise, command line 201 is coupled to the second input of NOR gate 1492, so that when command line 201 is activated, the output of NOR gate 1492 will be the inverse of the associated input from the counter 1496. Further, command line 202 is coupled to the second input of NOR gate 1493, so that when command line 202 is activated, the output of NOR gate 1493 will be the inverse of the associated input from the counter 1496.

The output of NOR gates 1491, 1492, and 1493 are coupled to the inputs of NOR gate 1494. Thus, the output of NOR gate 1494 will be a frequency corresponding to the status of the generator: either cut command, coagulate command, or automatic shutdown. If no command is selected, the output of NOR gate 1494 is fixed at high value.

The output of NOR gate 1494 is coupled through inverter 1495, resistor 3412 and potentiometer 3908 to ground. The wiper of potentiometer 3908 is connected through capacitor 4415 to one input of operational amplifier 1497, which input is connected to ground through capacitor 4416. Capacitor 4415 is also coupled to the second input of operational amplifier 1497 through capacitor 4414. The output of operational amplifier 1497 is coupled to ground through capacitor 4417 and loudspeaker 9906 in series. Therefore, the loudspeaker 9906 produces a tone for audible indication of generator status. The volume of the tone is varied by adjustment of potentiometer 3908.

FIG. 3 shows the mode control 105 and amplifiers 107, 109, 111, and 113. Command line 201 is coupled to the input of inverter 1611. Additionally, a 12 volt source is connected through resistor 3604 to the input of inverter 1611, so that the input of inverter 1611 is normally high value. The output of inverter 1611 is coupled to the input of NAND gate 1621, and to the input of NAND gate 1622.

When command line 201 is activated, the treating physician may select between the pure or blend modes by double pole/double throw switch 9901. Both wipers of switch 9901 are grounded. A 12 volt supply is connected through lamps 7905 and 7906 to the respective contacts for one wiper of switch 9901. Of the remaining two contacts of the second wiper of switch 9901, one contact is coupled to the input of inverter 1614, and the other contact is unconnected. A 12 volt supply is also coupled through resistor 3605 to the input of inverter 1614 and from that point through capacitor 4603 to ground. The output of inverter 1614 is coupled to an input of NAND gate 1621 and also coupled to the input of inverter 1613. The output of inverter 1613 is coupled to an input of NAND gate 1622.

Therefore, when command line 201 is activated (i.e., low value) and one wiper of switch 9901 makes contact with lamp 7905, the output of NAND gate 1621 is low and the output of NAND gate 1622 is high. Also, current is drawn through lamp 7905, indicating by light that the pure mode of operation has been selected. When command line 201 is low and switch 9901 makes contact with lamp 7906, the output of NAND gate 1621 is high and the output of NAND gate 1622 is low. Also, a lamp 7906 is lit, giving a visual indication that the blend mode of operation has been selected.

Similarly, when command line 202 is activated, the treating physician may select between the desiccate of fulgurate operations by double pole/double throw switch 9902. Both wipers of switch 9902 are grounded. A 12 volt supply is connected through lamps 7907 and 7908 to the respective contacts for one wiper of switch 9902. Of the remaining two contacts of the other wiper of switch 9902, one contact is coupled to the input of inverter 1616, and other contact is unconnected. A 12 volt supply is also coupled through resistor 3606 to the input of inverter 1616 and from that point through capacitor 4604 to ground. The output of inverter 1616 is coupled to the input of NAND gate 1624 and also coupled to the input of inverter 1615. The output of inverter 1615 is coupled to the input of NAND gate 1623.

Therefore, when command line 202 is activated (i.e., low value) and one wiper of switch 9902 makes contact with lamp 7907, the output of NAND gate 1623 is low and the output of NAND gate 1624 is high. Also, current is drawn through lamp 7907, indicating by light that the desiccate mode of operation has been selected. When command line 202 is low and switch 9901 makes contact with lamp 7908, the output of NAND gate 1623 is high and the output of NAND gate 1624 is low. Also, lamp 7908 is lit, giving a visual indication that the fulgurate mode of operation has been selected.

A typical amplifier 109 may be described as follows: The output of NAND gate 1622 is connected to the input of inverter 1632, and the output of inverter 1632 is connected to the anode of diode 6612. The output of NAND gate 1622 is also coupled to the input of inverter 1642, which supplies base current to the two transistors associated with the blend mode amplifier 109. The output of inverter of inverter 1642 is coupled through resistor 3612 to the base of transistor 2613. Transistors 2611, 2622, and 2613 operate in switching mode in this circuit; that is, when the output of inverter 1642 is high and current is supplied through the base resistors of the transistors, the collector and emitter of each transistor are shorted. When no base current is supplied, the collector and emitter are disconnected. The output of inverter 1642 also drives mode line 302.

The cathode of diode 6612 is connected through resistor 3608 to one side of potentiometer 3906. The other side of potentiometer 3906 is connected to resistor 3624 and capacitor 4607 in parallel. Capacitor 4607 is connected to ground. Resistor 3624 is coupled to the collector of transistor 2622. The emitter of transistor 2622 is connected to ground.

The wiper of potentiometer 3906 is connected through capacitor 4605 to ground, and the wiper is also connected to the collector of transistor 2613. The emitter of transistor 2613 is connected through resistor 3628 to the positive input of operational amplifier 1652.

Therefore, when the output of NAND gate 1622 is low indicating the blend mode of operation, the output of inverter 1632 is high. This voltage is connected to the potentiometer 3906. The voltage across potentiometer 3906 is established by the difference between the voltage supplied by inverter 1632 and the voltage across potentiometer 3624 and transistor 2622. In effect, potentiometer 3624 sets the minimum value of the output power range which may be controlled by potentiometer 3906.

The output of operational amplifier 1652 is connected through potentiometer 3636 and resistor 3632 to the negative input of operational amplifier 1652. This feedback loop establishes the gain of the operational amplifier configuration so that in effect the variable resistor 3636 establishes the maximum limit of the output power range controlled by the setting of potentiometer 3906. The output of operational amplifier 1652 is also connected through diode 6604 to voltage controlled main amplifier 800 via transmission line 502. The output of operational amplifier 1652 easily overcomes the forward bias voltage of diode 6604, but the reverse bias voltage of diode 6604 prevents any of the other three amplifiers which are coupled to line 502 from creating undesired feedback in operational amplifier 1652.

The amplifiers for the three remaining modes of operation of the invention operate in similar fashion.

Figure 4:
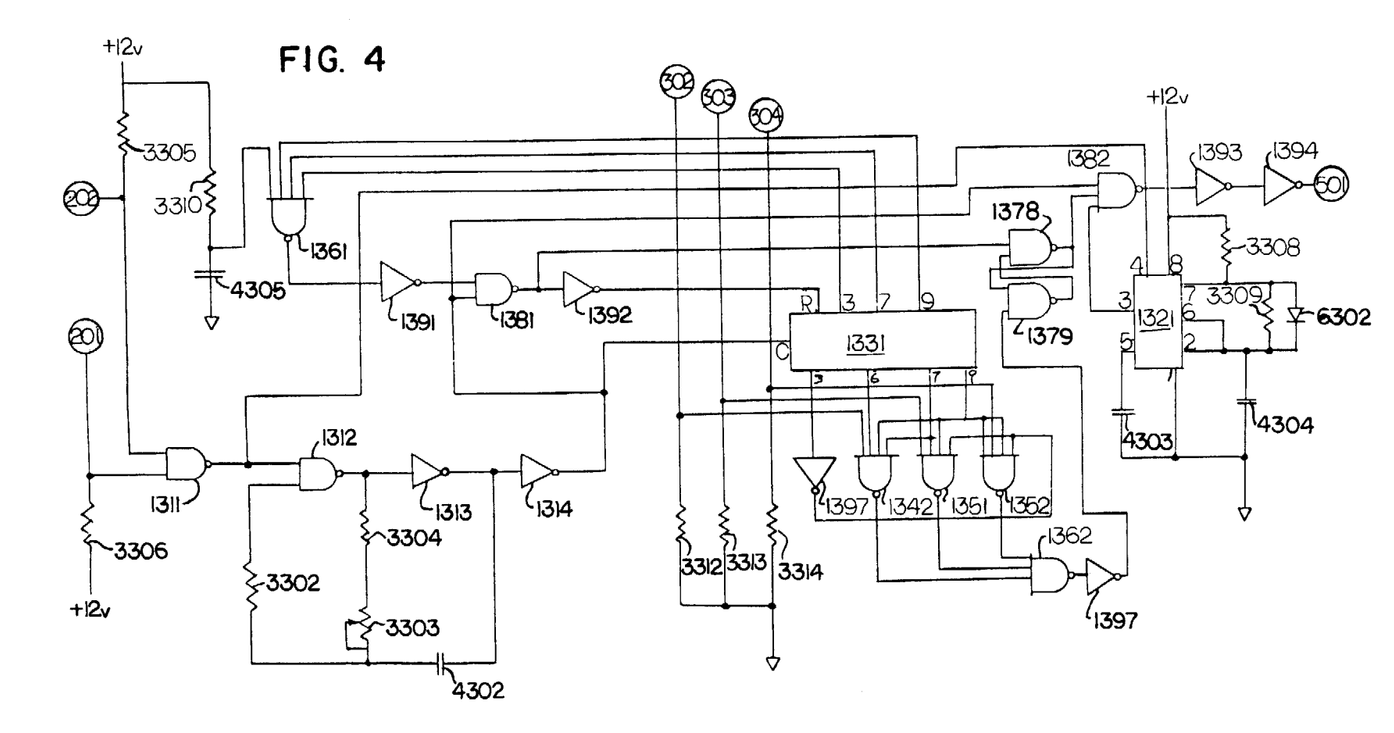
FIG. 4 is a circuit diagram of the high frequency oscillator 115, timer 117, variable frequency divider 119 and NAND gates 1311 and 1382 of FIG. 1.

FIG. 4 shows the high frequency oscillator 115, the variable frequency divider 119, the low frequency oscillator 117 and NAND gates 1311 and 1382.

Command line 201 is connected to one input of NAND gate 1311. A 12 volt supply is also connected through resistor 3306 to that input of NAND gate 1311, so that when command line 201 is not activated, the input will be high. Command line 202 is connected to another input of NAND gate 1311, and the 12 volt supply is also connected through resistor 3305 to this second input of NAND gate 1311 so that when command line 202 is not activated, the second output will also be high. However, if either command line is activated, the output of NAND gate 1311 will go high, activating the fixed high frequency oscillator 115 and the low frequency oscillator 117.

The output of NAND gate 1311 is connected to one input of NAND gate 1312. The output of NAND gate 1312 is coupled to the input of inverter 1313. The output of inverter 1313 is coupled through capacitor 4302 and resistor 3302 in series to the second input of NAND gate 1312. The output of NAND gate 1312 is also coupled through resistor 3304 and potentiometer 3303 in series to the resistor 3302. These elements comprise the fixed high frequency oscillator 115, the frequency of which be initially calibrated and set by adjustment of potentiometer 3303. The output of the oscillator is the output of the inverter 1313, which is coupled to the input of inverter 1314. The output of inverter 1314 is coupled to the counter input of integrated circuit 1331 and to one input of NAND gate 1382.

The output of NAND gate 1311 is also coupled to pin 4 of integrated circuit 1321. This integrated circuit is preferably a type 555 timer. A 12 volt supply is connected directly to pin 8 and through resistor 3308 to pin 7. Pin 7 is connected through resistor 3309 and diode 6302 in parallel to pins 6 and 2. Pin 2 is connected through capacitor 4304 to ground, pin 1 is connected directly to ground, and pin 5 is connected through capacitor 4303 to ground. Integrated circuit 1321 and associated elements comprise the low-frequency oscillator 117. The output of the low frequency oscillator is pin 3, which is connected to a second input of NAND gate 1382.

Integrated circuit 1331 is preferably a binary counter type 4040. The status of the output pins of integrated circuit 1331 presents a binary representation of the number of pulses of fixed high frequency oscillator 115. The three NAND gates, 1342, 1351, and 1352 vary the counter's function according to the mode selected by the operator, as represented by the status of the three mode lines 302, 303, and 304. The input of inverter 1399 is connected to pin 3 of integrated circuit 1331. The inputs of NAND gate 1342 are connected to the mode line 302 and pins 6, 7, and 9 of integrated circuit 1331. The inputs of NAND gate 1351 are connected to mode line 303, to pins 7 and 9, and to the output of inverter 1399. The inputs of NAND gate 1352 are connected to mode line 304, to pin 9 (twice) and to the output of inverter 1399. The output of each of these three NAND gates are connected to the input of NAND gate 1362, and the output of NAND gate 1362 is connected to the input of inverter 1377.

NAND gates 1378 and 1379 are configured to act as a set-reset flipflop. The output of NAND gate 1378 is coupled to one input of NAND gate 1379, and the output of NAND gate 1379 is coupled to one input of NAND gate 1378. The output of inverter 1377 is connected to the second input of NAND gate 1379 and the output of NAND gate 1381 is connected to the second input of NAND gate 1378. The output of NAND gate 1378 is also connected to a third output of NAND gate 1382.

Pins 3, 7, and 9 of integrated circuit 1331 are connected to three inputs of NAND gate 1361. The fourth input of NAND gate 1361 is coupled through resistor 3310 to a 12 volt supply, and through capacitor 4305 to ground. The output of NAND gate 1361 is connector to the input of inverter 1391. The output of inverter 1391 is connected to one input of NAND gate 1381 and the output of inverter 1314 is connected to the second input of NAND gate 1381. The output of NAND gate 1381 is coupled to the input of inverter 1392, and the output of inverter 1392 is coupled to the reset pin of the integrated circuit 1331.

Integrated circuits 1331, NAND gates 1378 and 1379 and circuit elements connected therebetween, comprise the variable frequency divider 119.

Therefore, when the high frequency oscillator is operating, integrated circuit 1331 will count the number of oscillations until the output of NAND gate 1381 goes low and integrated circuit 1331 is reset, which occurs when pins 3, 7, and 9 of integrated circuit 1331 are all high, and the output of inverter 1314 is low. The pulses of fixed high frequency oscillator 115 will pass through NAND gate 1382 and inverters 1393 and 1394 to the main voltage controlled amplifier so long as the outputs of the low frequency oscillator 117 and variable frequency divider 119 are high. The output of variable frequency divider 119, which is the output of inverter 1377, will go high after an output pulse group size determined by the integrated circuit 1331 and the NAND gate selected by the activated mode line. The pure cut mode selects no NAND gate and so, in this mode, the output of NAND gate 1378 is never reset. Blend mode line 302 activates NAND gate 1342, which resets the output of NAND gate 1378 after 7 pulses of the high frequency oscillator. Desiccate mode line 303 activates NAND gate 1351, which resets the output of NAND gate 1378 after 3 pulses. Fulgurate mode line 304 activates NAND gate 1352, which resets the output of NAND gate 1378 after 1 pulse. The output of NAND gate 1378 then remains low and the counter continues to run until 19 pulses are counted, at which time the counter is reset and the output of NAND gate 1378 is set to high value. The output waveforms of the pure cut, blend, desiccate, and fulgurate modes are illustrated in FIGS. 9, 10, 11, and 12, respectively. Therefore, the output of variable frequency divider 119 comprises a low voltage portion during which output pulses are generated, followed by a high voltage during which output pulses are suppressed. In the pure cut mode, the ratio of high voltage length to low voltage length is 0:20; during blend mode, the ratio 13:7; during dessicate, the ratio is 17:3; and during fulgurate mode, the ratio is 19:1.

Figure 5:
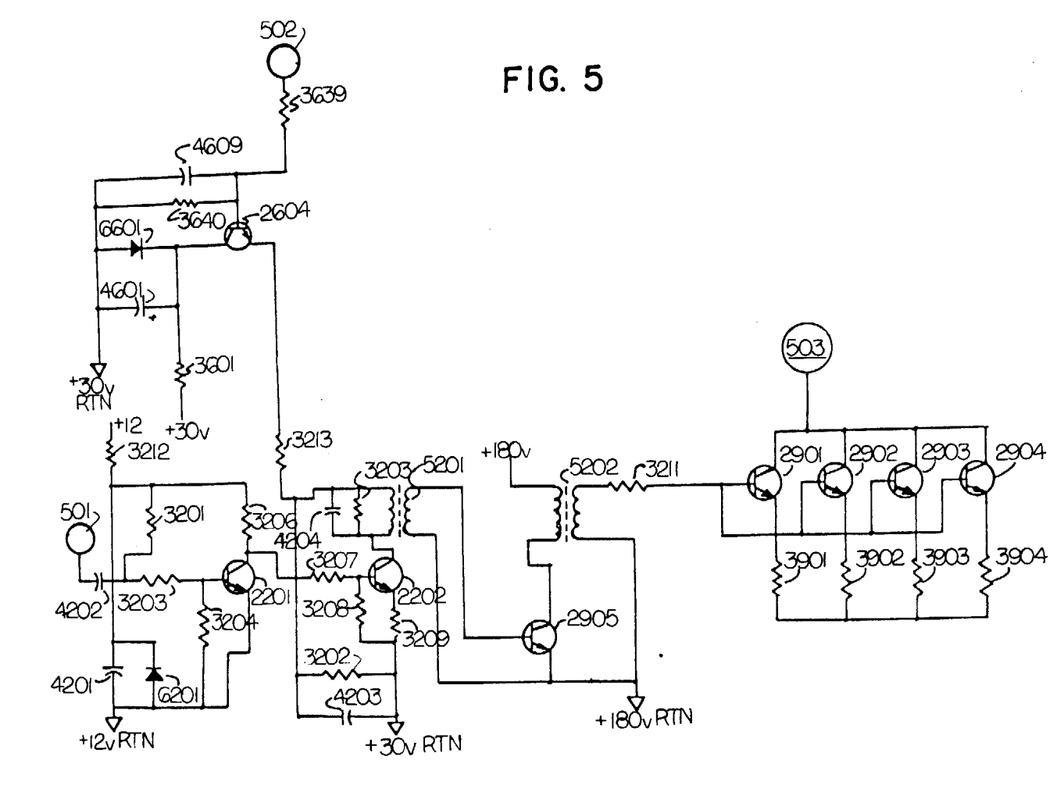
FIG. 5 is a circuit diagram of the voltage controlled main amplifier 121 of FIG. 1.

FIG. 5 shows the voltage-controlled main amplifier 200. A 12 volt supply is connected through resistors 3212 and 3206 in series to the collector of transistor 2201. The 12 volt supply is also coupled through resistors 3212, 3201 and 3203 in series to the base of transistor 2201. The base of transistor 2201 is also connected through resistor 3204 to a 12 volt supply return bus. The 12 volt supply is also connected through resistor 3212 to capacitor 4201 in parallel with zener diode 6201, and this capacitor and zener diode are connected to the 12 volt return bus.

The output of NAND gate 1392 is connected through inverters 1393 and 1394 to line 501. Line 501 is coupled through capacitor 4202 and resistor 3203 in series to the base of transistor 2201. Capacitor 4202 blocks spurious D.C. current from reaching the base of the transistor 2201 and passing through main amplifier 200 to the patient. The emitter of transistor 2201 is connected directly to the 12 volt return bus.

The output amplifiers 107, 109, 111, and 113 are connected through line 502 and resistor 3639 in series to the base of transistor 2604. The base of transistor 2604 is also coupled through capacitor 4609 and resistor 3640 connected in parallel to the 30 volt return bus. The collector of transistor 2604 is connected through zener diode 6601 in parallel with capacitor 4601 to the 30 volt return bus, and the collector of transistor 2604 is also connected through resistor 3601 to the 30 volt supply.

The collector of transistor 2201 is connected through resistor 3207 to the base of transistor 2202, and the base of transistor 2202 is also connected through resistor 3208 to the 30 volt return bus. The emitter of transistor 2202 is connected through resistor 3209 to the 30 volt return bus also.

The emitter of transistor 2604 is connected to the gain control stage of the voltage-controlled main amplifier 200. The emitter is coupled through resistor 3213 to capacitor 4203 in parallel with resistor 3202 to the 30 volt supply return bus. The emitter of transistor 2604 is also connected through resistor 3213 to capacitor 4204, resistor 3205, and the primary winding of isolation transformer 5201 in parallel, and through these elements to the collector of transistor 2202.

Capacitor 4204, resistor 3205, and transformer 5201 form a parallel resonant circuit which produces the voltage spike of each output pulse group. While FIGS. 9 through 12 show the voltage spike at the beginning of the output pulse group, the voltage spike can be placed anywhere in the pulse group. Any of the pulses in the pulse group having a high voltage can ionize the current path provided on the current drive portion if the time lag between spikes is not excessive. Subsequent pulses of the group or a following group establish a signal frequency outside the resonant frequency range of the resonant circuit to produce lower voltage across the secondary winding of transformer 5201 than does the spike pulse of each group.

Thus, the voltage spike of each output pulse group achieves a high ratio of peak power to RMS power, which ratio is referred to hereinafter as crest factor ratio. The crest factor ratio obtained in the present invention for the pure cut mode ranges from 3:1 to 5:1; blend mode 5:1 to 8:1; desiccate mode 5:1 to 8:1; and fulgurate mode 14:1 to 18:1. A high crest factor ratio is desirable as an efficient cause of ionization without excessive tissue heating. The highest crest factor ratio known to be achieved in the prior art is 12:1 to 13:1 for the coagulate mode.

Figure 14:
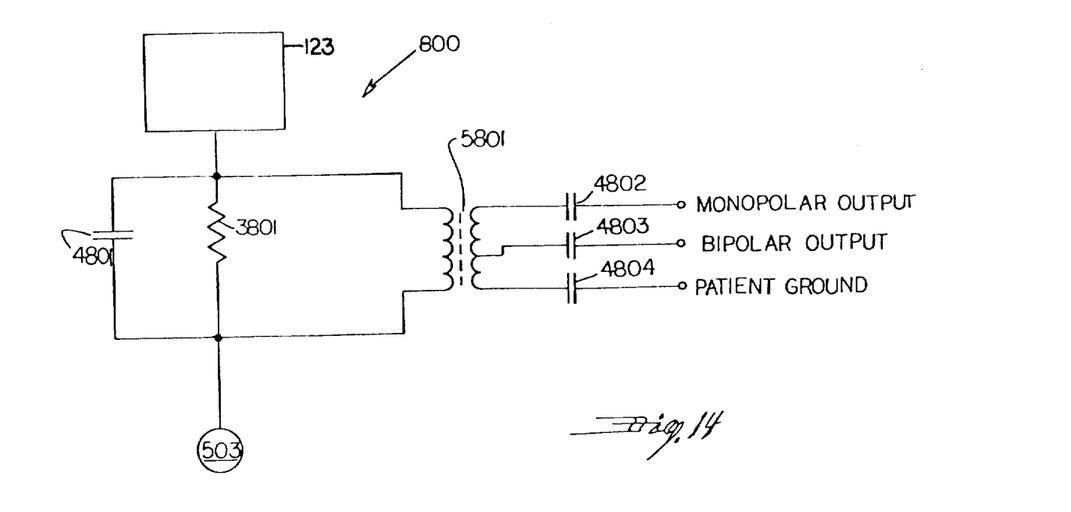
FIG. 14 is a circuit diagram for a patient isolation for the electrosurgical generator.

One side tap of the secondary winding of transformer 5201 is connected to the base of transistor 2905, and the other side tap is connected to the 180 volt return bus. The emitter of transistor 2905 is also connected to the 180 volt return bus. The collector of transistor 2905 is connected through the primary winding of isolation transformer 5202 to the 180 volt supply. One side tap of the secondary winding of transformer 5202 is connected to the 180 volt return bus, and the other side tap is connected through resistor 3211 to the constant-current amplifier stage of the voltage-controlled main amplifier 200. Resistor 3211 is connected to the bases of transistors 2901, 2902, 2903, and 2904. The emitters of transistors 2901, 2902, 2903, and 2904 are coupled to one another through resistors 3901, 3902, 3903, and 3904, respectively. The collectors of transistors 2901, 2902, 2903 and 2904 are coupled to one another and through line 503 and output isolation 800 to patient output terminals. FIG. 14 illustrates one embodiment of the output isolation 800. The primary winding of transformer 5801 is connected in parallel to resistor 3801 and capacitor 4801. Line 503 is connected through this resonant circuit to 180 volt power supply 123. One side tap of the transformer 5801 secondary winding is connected through capacitor 4802 to the monopolar output terminal of the electrosurgical generator. Another side tap is connected through capacitor 4804 to the patient return terminal of the electrosurgical generator. The center tap of transformer 5801 is connected through capacitor 4803 to the bipolar output terminal of the electrosurgical generator.

Figure 15:
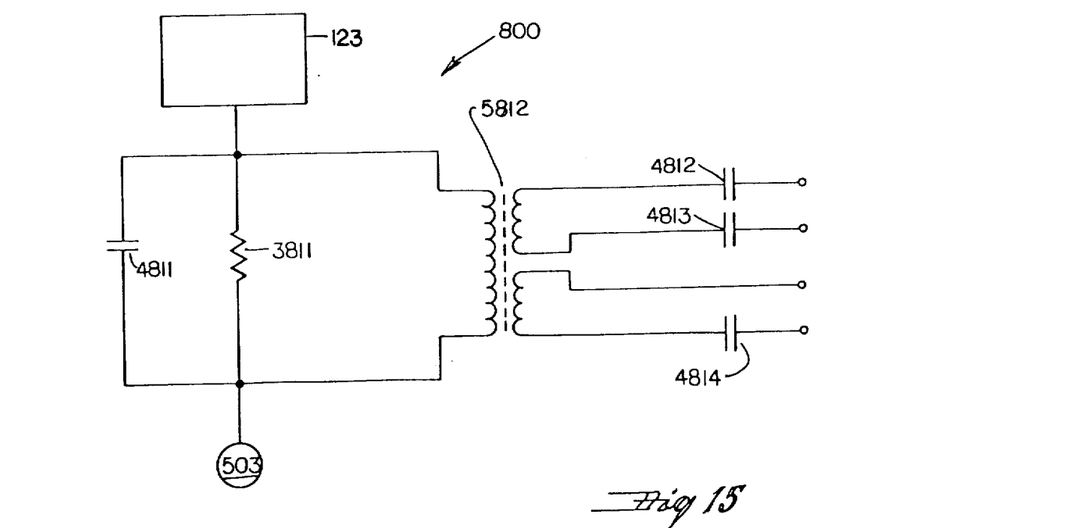
FIG. 15 is a circuit diagram for an alternate patient isolation for the electrosurgical generator.

FIG. 15 illustrates an alternative output isolation 800 with reduced common mode current between the monopolar and bipolar output terminals. Line 503 is coupled through capacitor 4811, resistor 3811 and the transformer 5812 primary winding in parallel to a 180 volt supply. Transformer 5812 has two separate secondary windings. The side taps of one secondary are connected through capacitors 4812 and 4813 respectively to active and dispersive monopolar output terminals, respectively. The other transformer 5812 secondary winding side taps are coupled through capacitor 4814 to one bipolar output terminal and directly to the other bipolar output terminal respectively.

Figure 6:
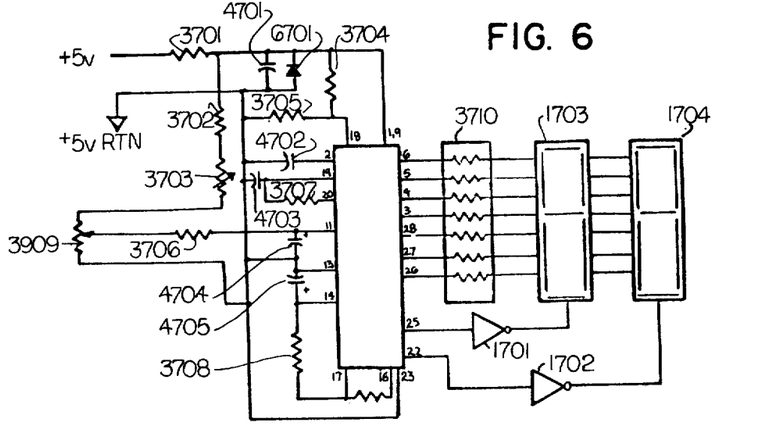
FIG. 6 is a circuit diagram of a digital display of the output level of the output control amplifiers of FIG. 3.

FIG. 6 shows a display device for digital display of the output level of the electrosurgical generator. In the preferred form of the invention, two such displays are included, one for each of the two command groups. Potentiometer 3909 of the first such display device is ganged to potentiometer 3906 for the cut command group, and potentiometer 3909 of the second such device is ganged to potentiometer 3907 for the coagulate command group.

A 5 volt supply is connected through resistors 3701 and 3702 and variable resistor 3703 in series to the potentiometer 3909, and through the potentiometer to the 5 volt return bus. The wiper of potentiometer 3909 is connected through resistor 3706 to pin 11 of integrated circuit 1700. This integrated circuit is preferably of a type ADD 3501 CCN analog-to-digital converter. The 5 volt supply is also connected through resistor 3701 to pins 1 and 9 of integrated circuit 1700. Pins 1 and 9 are connected through resistor 3704 to pin 18, and pin 18 is connected through resistor 3705 to the 5 volt return bus. Pin 2 is connected through capacitor 4702 to the 5 volt return bus, pin 19 is connected through resistor 3707 to pin 20, and pin 19 is also connected through capacitor 4703 to the 5 volt return bus. Pin 11 is connected through capacitor 4704 to pin 15, and pin 15 is connected to the 5 volt return bus. Pin 14 is connected through capacitor 4705 to the 5 volt return bus, and pin 14 is also coupled through resistor 3708 to pin 17. Pin 17 is connected through resistor 3709 to pin 16. Pin 25 is coupled directly to the 5 volt return bus.

The output of pins of integrated circuit 1700 are pins 6, 5, 4, 3, 28, 27 and 26. These pins are connected through resistor pack 3710 to the segment pins of the 7-segment displays 1703 and 1704 in parallel. Pin 23 of the integrated circuit 1700 is connected to the input of inverter 1701, and the output of inverter 1701 is connected to the drive pin of display 1703. Pin 22 of integrated 1700 is connected to the input of inverter 1702, and the output of inverter 1702 is connected to the drive pin of display 1704.

Figure 13:
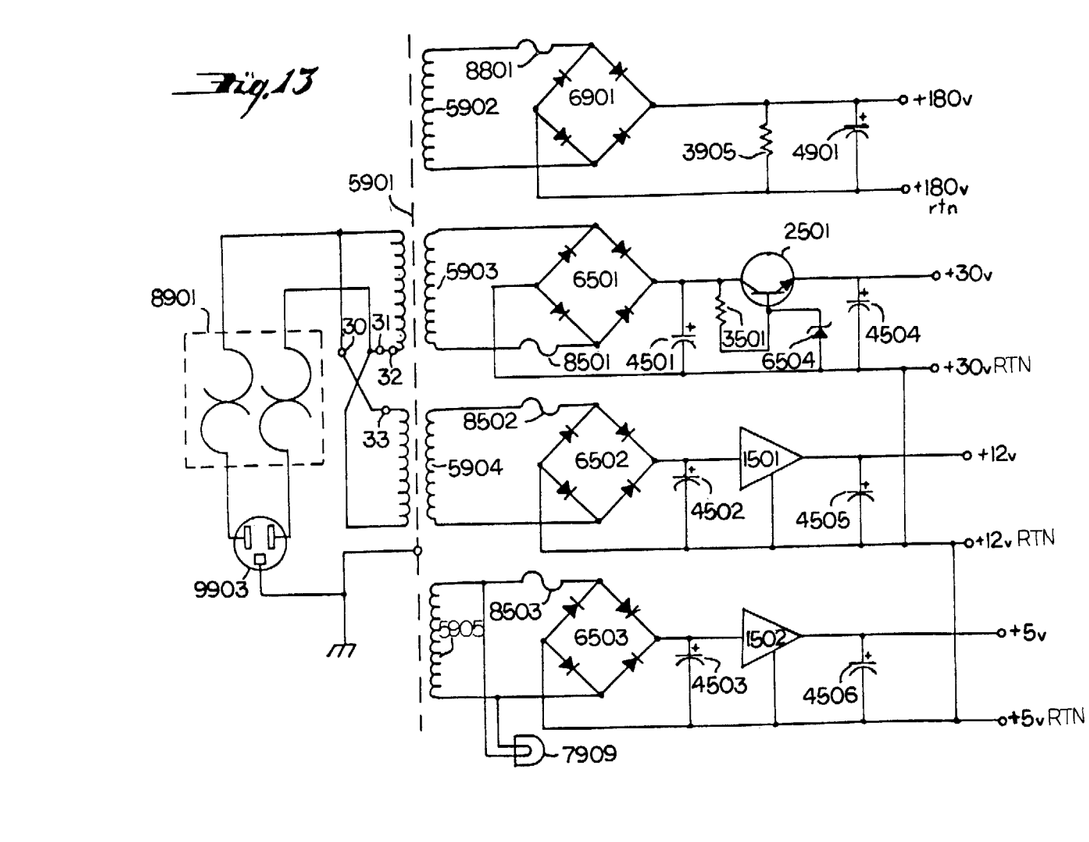
FIG. 13 is a circuit diagram for a power supply for the electrosurgical generator.

FIG. 13 shows a power supply circuit for the electrosurgical generator. The power supply is designed to be supplied with wall current through standard 3-wire plug 9903. The ground pin of plug 9903 is coupled to the core of power transformer 5901, and the two power pins of plug 9903 are connected through the dual-pole circuit breaker 8901 to the side taps of the primary winding of the power transformer 5901. The primary winding is shown wired to accept 110 volt input, however, it may be rewired to accept 220 volt input by breaking the connections at points 30 and 31 and making a connection between points 32 and 33.

Transformer 5901 has four secondary windings. One side tap of secondary 5902 is coupled directly to one input of full-wave bridge rectifier 6901, and the other side tap is coupled through fuse 8801 to the second input of bridge 6901. The negative output of bridge 6901 is coupled through resistor 3905 and capacitor 4901 in parallel to the positive output of bridge 6901. The positive output of bridge 6901 supplies 180 volts direct current, and the negative output is the return line for this voltage.

One side tap of the secondary 5903 is connected directly to one input of full-wave bridge rectifier 6501, and the other side tap of the secondary is coupled through fuse 8501 to the second input to bridge 6501. The positive output of bridge 6501 is coupled through capacitor 4501 to the negative output of the bridge, and the positive output is also coupled through resistor 3501 to the base of the transistor 2501. The positive output of bridge 6501 is also coupled directly to the collector of transistor 2501. The base of transistor 2501 is coupled through zener 6504 to the negative output of bridge 6501, and the emitter of transistor 2501 is coupled through capacitor 4504 to the negative output. The emitter of transistor 3501 provides 30 volts direct current, which is returned to the negative output of bridge 6501.

One side tap of secondary 5904 is connected through fuse 8502 to one input of full-wave bridge rectifier 6502, and the other side tap of the secondary is connected directly to the second input of bridge 6502. The positive output of bridge 6502 is coupled directly to the input of voltage regulator 1501, and through capacitor 4502 to the negative output of bridge 6502. The ground of voltage regulator 1501 is coupled directly to the negative output of the bridge, and the positive output of the voltage regulator is coupled through capacitor 4505 to the negative output of the bridge. The positive output of voltage regulator 1501 provides 12 volts direct current, which may be returned to the negative input of bridge 6502.

One side tap of the secondary 5905 is connected through fuse 8503 to one input of full-wave bridge rectifier 6503, and the other side tap of the secondary is coupled directly to the second input of bridge 6503. The positive output of bridge 6503 is coupled directly to the input of voltage regulator 1502, and through capacitor 4503 to the negative output of bridge 6503. The ground of voltage regulator 1502 is coupled directly to the negative output to the bridge, and the positive output of voltage regulator 1502 is coupled through capacitor 4506 to the negative output of the bridge. The positive output of the voltage regulator supplies 5 volts direct current, which may be returned to the negative output of the bridge.

The negative output of the bridges 6501, 6502 and 6503 are coupled directly to one another. The side taps of secondary 5905 are coupled through lamp 7909 to give indication of circuit breaker status.

In a working embodiment of this invention, the following components were utilized. It should be appreciated however that the list of components is for illustration only and the invention is not meant to be limited thereto.

Integrated Circuits

Type 4023 three-input NAND gates: 1461, 1462, 1481, 1482 and 1483.
Type 4012 quad-input NAND gates: 1341, 1342, 1351, 1361, 1362 and 1382.
Type 4049 inverters: 1391, 1392, 1393, 1394, 1399, 1431, 1432, 1434, 1435, 1436, 1471, 1472, 1473, 1611, 1612, 1613, 1614, 1615, 1616, 1631, 1632, 1633, 1634, 1641, 1642, 1643, 1644, 1645, 1646.
Type 4011 NAND gates: 1311, 1312, 1313, 1314, 1621, 1622, 1623 and 1624.
Type 4001 NOR gates: 1441, 1442, 1443, 1444, 1451, 1452, 1453, 1491, 1493 and 1492.
Type 55 timers: 1321
Type 556 timers: 1411 and 1412
Type 4N28 opto-isolators: 1421 and 1422
Type 4025 three-input NOR gates: 1494 and 1495
Type 4040 binary counters: 1331 and 1496
Type 3900 operational amplifiers: 1651, 1652, 1653 and 1654
Type 380N audio amplifiers: 1497
Type 75492 inverters: 1701 and 1702
Type ADD 3501 CCN analog-to-digital converters: 1700
7-segment displays: 1703 and 1704
Type LM340T12 voltage regulator: 1501
Type LM340T5 voltage regulator: 1502

Capacitors 10 uF, 35 v; 4201, 4301, 4409, 4417 and 4702
0.1 uF, 50 v: 4202, 4415, 4416, 4603, 4604, 4605, 4606, 4607, 4608 and 4609
50 uF, 50 v: 4203, 4401, 4504, 4505, and 4506
200 uF, 500 v: 4204
0.01 uF, 100 v: 4303, 4304, 4403, 4404, 4405, 4406, 4407, 4408, 4410, 4411, 4412, 4413, 4418, 4419, 4420 and 4421

100 pF, 200 v: 4302
0.1 uF, 35 v: 4306
0.001 uF, 200 v: 4414
47 uF, 20 v: 4701
220 pF, 200 v: 4703
0.47 uF, 35 v: 4704 and 4705
22000 pF, 500 v: 4801
12000 pF, 500 v: 4811
0.01 uF, 3000 v: 4802, 4803 and 4804
500 mF: 4901
10 uF, 50 v: 4601 and 4602
150 uF, 50 v: 4501
500 uF, 35 v: 4502 and 4503
0.0047 uF, 3000 v: 4812, 4813 and 4814

Transistors

2N222A: 2201 and 2401
2N6044: 2202, 2501 and 2604
IR 519: 2905
MPQ2222: 2402, 2403, 2404, 2602, 2603, 2612, 2622, 2632, 2613, 2623, and 2633
DTS 430: 2901, 2902, 2903 and 2904

Resistors (all ¼ watt, 5% unless otherwise specified)

22K: 3201, 3302 and 3310
10K: 3202, 3208, 3305, 3306, 3311, 3312, 3313, 3314, 3407, 3408,
3409, 3414, 3415, 3418, 3603, 3604, 3605, 3606, 3608, 3611, 3612,
3613, 3614, 3616, 3618, 3619, 3620, 3621, 3622 and 3704
1K: 3203, 3206, 3404, 3410, 3411, 3412, 3413, 3416, 3417, 3420, 3420 and 3639
47K: 3204 and 3905
680: 3205 and 3406
47: 3207
10: 3209, 3210 (1 watt), 3211 (10 watt)
27: 3212, 3213 and 3601
15: 3301 (½ watt), 3401 (½ watt), 3405 (½ watt), 3602 (½ watt) and 3701
2.7K: 3004
330K: 3308
220K: 3309, 3627, 3628, 3629, 3630, 3634 and 3709
6.8K: 3402 and 3707
27K: 3403 and 3419
2.2K: 3501
100K: 3631, 3632, 3633, 3706 and 3708
33K: 3702
8.2K: 3705
100: 3710
500: 3801 (10 watt)
1 (25 watt): 3901, 3902, 3903 and 3904

Diodes

Zener 1N4744Z: 6201
Zener 1N4751A: 6504
1N4001: 6302, 6402, 6403, 6404, 6405, 6603, 6604, 6605, 6606, 6607
IN914: 6611, 6612, 6613 and 6614
Zener 1N4735A: 6701
Zener 1N4752A: 6602
Full-wave bridge rectifier, 2 amp: 6501, 6502 and 6503
Full-wave bridge rectifier, 12 amp: 6901

Fuses 1 amp: 8501 and 8502
½ amp: 8503
8 amp: 8801
7.5 amp circuit breaker, dual pole: 8901

In preparation for operation of the invention a return electrode, preferably of relatively large area, should be applied to the patient and connected to the patient return terminal of the electrosurgical generator output. Also, the electrode scalpel should be plugged into the monopolar output or the two bipolar outputs as may be appropriate for the particular electrode scalpel configuration.

Operation of the invention is begun by turning on circuit breaker 8901 to provide power to the power supply of the electrosurgical generator. Mode switches 9901 and 9902 are then adjusted to preset the modes to be activated during the course of surgery by selection of either the cut command or the coagulate command. The power levels to be applied during each mode of operation are then set by adjusting the potentiometers 3906 and 3907 which settings can be read from the dual digital display systems.

To begin surgery, either of switches 510 or 512 may be closed to activate the cut command group, or either of switches 511 or 513 may be closed to activate the coagulate command group. Output to the electrode scalpel can be interrupted at any time without adjusting the circuit breaker 8901 by opening the switch which has been closed or by closing a switch activating the opposite command group. In the latter case, or if the thermostat 9903 detects overheating of the output transistors, then the command control automatically activates the appropriate lamp and changes the output frequency of the tone generator to indicate an automatic shutdown of operation. If automatic shutdown is not encountered, then the command control activates the command line corresponding to the command switch which has been closed.

In response to the activation of the command line, both the high-frequency oscillator 115 and the timer 117 begin operation. Also, the mode control 105 activates a mode line within the activated command group corresponding to the preset status of switches 9901 or 9902. The activated mode line in turn activates a particular division function of the variable frequency divider 119 and a corresponding one of the four output level amplifiers 107, 109, 111 or 113. The activated output level amplifier emits a signal corresponding to the adjustment already made to potentiometers 3906 or 3907.

The outputs of the high-frequency oscillator 115, the timer 117 and the variable frequency divider 119 are fed to NAND gate 1382. The output of high-frequency oscillator 115 is interrupted by the variable frequency divider 119 to produce a signal causing tissue destruction corresponding to the mode selected by the command switch and the mode switch. The timer 117 interrupts the output of high-frequency oscillator 115 to provide a duty cycle of operation for protection of power supplies and output transistors. The output of NAND gate 1382 is then amplified by main amplifier 200, the gain of which is set by the activated output level amplifier. The voltage across the primary winding of output transformer 5801 is equal to the level of the DC voltage supply 123 minus the output signal of amplifier 200. The current generated through the secondary winding of output transformer 5801 passes through a blocking capacitor to the electrode scalpel and then may be returned either through the patient return or to the bipolar output terminal and the blocking capacitor coupled thereto.

During the surgical procedure, should the physician wish to switch between modes of operation within a command group, only the appropriate mode switch 9901 and 9902 need be manipulated. If one command group is deactivated and the other is started, then the mode control automatically activates the appropriate mode line corresponding to the preset mode switch 9901 and 9902. The power levels of the output may also be continually adjusted by manipulating potentiometers 3906 and 3907.

In the foregoing description, the invention has been described with reference to a particular embodiment, although it is to be understood that the specific details shown are merely illustrative and that the invention may be carried out in other ways without departing from the true spirit and scope of the following claims.

What is claimed is:

1. A generator for electrosurgery comprising first and second command switches for selecting command status of operation; a command control means coupled to said first and second command switches for preventing simultaneous activation of said first and second command switches; a first mode switch for selecting a mode of operation when the first command switch is activated; a second mode switch for selecting a mode of operation when the second command switch is activated; a mode control means coupled to said first and second mode switches for determining the mode of operation indicated by said first and second command switches and said first and second mode switches, said command control means being coupled to said mode control means by first and second command lines; first, second, third and fourth voltage amplifiers, each said voltage amplifier being coupled to said mode control means so that one of said voltage amplifiers corresponding to the mode of operation indicated by said first and second mode switches and said first and second command switches is activated by said mode control means; a first NAND gate having two inputs, the inputs of said first NAND gate being coupled respectively to the said first and second command lines; high frequency oscillator means and low frequency oscillator means coupled to the output of said first NAND gate so that said high and low frequency oscillator means are activated by said first NAND gate when either command line is activated; a three-input NAND gate, the output of said high frequency oscillator means being coupled to a first input of said three-input NAND gate, the output of said low frequency oscillator means comprising a duty cycle interrupt signal and being coupled to a second input of said three-input NAND gate, variable frequency divider means, the output of said high frequency oscillator means also being coupled to said variable frequency divider means, said variable frequency divider means also being coupled to the output of said mode control means, the output of said variable frequency divider means being coupled to the third input of said three-input NAND gate and comprising a waveform interrupt signal comprised of a high voltage portion and a low voltage portion, the wave-length of said waveform interrupt signal being an integer multiple of the wavelength of the output of said high frequency oscillator means, the ratio of the length of said high voltage portion to the length of said low voltage portion being altered by said variable frequency divider means corresponding to the mode of operation indicated by said first and second mode switches and said first and second command switches; a voltage controlled main amplifier means, the output of said three-input NAND gate being coupled to the input of said voltage controlled main amplifier means and comprising groups of pulses, said voltage controlled main amplifier means including means for selectively increasing the amplitude of a pulse of each said group of pulses from said three-input NAND gate, said voltage controlled main amplifier means being coupled to said first, second, third and fourth voltage amplifiers so that said voltage amplifiers control the output level of said voltage controlled main amplifier means; a DC voltage supply and an isolation transformer means, the output of said voltage controlled main amplifier means being coupled through the primary winding of said isolation transformer means to said DC voltage supply, said isolation transformer means having first and second secondary windings, the side taps of said first secondary winding being coupled through first and second blocking capacitors, respectively, to first and second output terminals for monopolar operation, one side tap of said second secondary winding being coupled through a third blocking capacitor to a third terminal for bipolar operation, the other side tap of said second secondary winding being coupled directly to a fourth output terminal for bipolar operation.

2. The apparatus as claimed in claim 1 including a plurality of gain control means coupled to each of said first, second, third and fourth amplifiers for adjustment of the output voltage of said amplifiers.

3. The apparatus as claimed in claim 2 in which said first and second amplifiers are coupled to one of said gain control means, and said third and fourth amplifiers are coupled to a second of said gain control means.

4. The apparatus as claimed in claim 1 wherein each of said first and second command control switches comprises a plurality of switches connected in parallel.

5. The apparatus as claimed in claim 1 including isolation means comprising a power supply and opto-isolator, said first and second command switches being coupled to said isolation means and said isolation means being coupled to said command control means.

6. The apparatus as claimed in claim 1 wherein said voltage controlled main amplifier means includes an output stage, said output stage comprising a constant-current amplifier.

7. The apparatus as claimed in claim 6 wherein said output stage functions as a constant-current amplifier over a human tissue impedance range of 25 to 2000 ohms.

8. The apparatus as claimed in claim 6 wherein the input of said output stage includes an isolation transformer.

9. The apparatus as claimed in claim 1 including first and second display means for displaying the power output level corresponding to each of said first and second command switches.

10. The apparatus as claimed in claim 1 wherein the initial pulse of each group of pulses has a crest ratio in the range of 3:1 to 18:1.

11. The apparatus as claimed in claim 1 wherein said means for selectively increasing the amplitude of a pulse of each said group of pulses is a resonant circuit, said resonant circuit comprising a resistor, capacitor and transformer coupled in parallel, said circuit being tuned to a resonant frequency not equal to the frequency of said high-frequency oscillator means.

12. The apparatus as claimed in claim 1 wherein said high-frequency oscillator means produces an output frequency of 450 kilohertz.

13. The apparatus as claimed in claim 1 wherein said low frequency oscillator means produces an output frequency of 5 kilohertz.

14. The apparatus as claimed in claim 1 wherein said ratio of the length of said high voltage portion to the length of said low voltage portion varies in the range of 0:20 to 19:1.

* * * * *